United States Patent
Vanheule et al.

(10) Patent No.: US 9,822,238 B2
(45) Date of Patent: Nov. 21, 2017

(54) COMPOSITIONS COMPRISING TETRAHYDROFURFURYL AND ALKOXYLATED ALKYL ESTERS AS PLASTICISERS FOR BIODEGRADABLE RESINS

(71) Applicant: Proviron Holding N.V., Hemiksem (BE)

(72) Inventors: Jose Vanheule, Hemiksem (BE); Johan Declerck, Hemiksem (BE); Sonja Stankovic, Hemiksem (BE)

(73) Assignee: PROVIRON HOLDING N.V., Hemiksem (BE)

( * ) Notice: Subject to any disclaimer, the term of this patent is extended or adjusted under 35 U.S.C. 154(b) by 0 days.

(21) Appl. No.: 15/104,645

(22) PCT Filed: Dec. 4, 2014

(86) PCT No.: PCT/EP2014/025023
§ 371 (c)(1),
(2) Date: Jun. 15, 2016

(87) PCT Pub. No.: WO2015/090620
PCT Pub. Date: Jun. 25, 2015

(65) Prior Publication Data
US 2016/0319101 A1 Nov. 3, 2016

(30) Foreign Application Priority Data

Dec. 20, 2013 (BE) .................................. 2013/0862

(51) Int. Cl.
*C08K 5/1535* (2006.01)
*C08K 5/11* (2006.01)
*C07D 307/12* (2006.01)

(52) U.S. Cl.
CPC .......... *C08K 5/1535* (2013.01); *C07D 307/12* (2013.01); *C08K 5/11* (2013.01)

(58) Field of Classification Search
CPC ............................. C08K 5/1535; C07D 307/12
USPC ........................................................ 524/111
See application file for complete search history.

(56) References Cited

U.S. PATENT DOCUMENTS

| | | | | |
|---|---|---|---|---|
| 1,989,701 A | * | 2/1935 | Lawson | C08K 5/10 106/162.72 |
| 2015/0033985 A1 | * | 2/2015 | Kavanagh | C07D 405/14 106/170.29 |
| 2015/0322310 A1 | * | 11/2015 | Taleyarkhan | C09J 167/04 428/431 |

FOREIGN PATENT DOCUMENTS

| | | |
|---|---|---|
| JP | 2005023091 A | 1/2005 |
| WO | 2013148255 A1 | 10/2013 |

OTHER PUBLICATIONS

International Preliminary Report on Patentability, dated Jun. 21, 2016, from counterpart International Application No. PCT/EP2014/025022, filed on Dec. 4, 2014. Four pages.
International Preliminary Report on Patentability, dated Jun. 21, 2016, from counterpart International Application No. PCT/EP2014/025023, filed on Dec. 4, 2014. Four pages.
International Search Report and Written Opinion of the International Searching Authority, dated Feb. 27, 2015, from International Application No. PCT/EP2014/025022, filed on Dec. 4, 2014. Six pages.
International Search Report and Written Opinion of the International Searching Authority, dated Feb. 27, 2015, from International Application No. PCT/EP2014/025023, filed on Dec. 4, 2014. Six pages.

* cited by examiner

*Primary Examiner* — Hui Chin
(74) *Attorney, Agent, or Firm* — HoustonHogle LLP

(57) ABSTRACT

The present invention refers to a composition comprising tetrahydrofurfuryl and alkoxylated alkyl esters and their use as plasticizers in biodegradable resins, more in particular, in a biodegradable aliphatic polyester resin comprising polylactic acid. In a preferred embodiment the composition comprises a tetrahydrofurfuryl butyldiglycolate ester. The invention also refers to a biodegradable resin composition, more in particular, comprising homo- or co-polymers of polylactic acid and comprising such compositions.

11 Claims, No Drawings

COMPOSITIONS COMPRISING TETRAHYDROFURFURYL AND ALKOXYLATED ALKYL ESTERS AS PLASTICISERS FOR BIODEGRADABLE RESINS

RELATED APPLICATIONS

This application is a §371 National Phase Application of International Application No. PCT/EP2014/025023, filed on Dec. 4, 2014, which claims priority to Belgium Patent Application No. 2013/0862, filed on Dec. 20, 2013, both of which are incorporated herein by reference in their entirety.

FIELD OF THE INVENTION

The present invention relates to a novel composition of an ester mixture suitable for use as plasticiser in biodegradable polymers such as e.g. a biodegradable aliphatic polyester resin.

More in particular the invention relates to a mixed ester that can be obtained from the esterification of an aliphatic polycarboxylic acid with specific mixtures of alcohols. These products exhibit specific properties in relation with the compatibility with the biodegradable resin composition. The selection of the alcohols and the aliphatic polycarboxylic acid yields products of fully or partially biological origin.

In this way they help to increase the sustainability of the final application.

BACKGROUND OF THE INVENTION

Nowadays, petroleum-based polymers are widely used as traditional plastics in, for example, packaging and other consumables. These products, however, have various disadvantages, in particular, the accumulation of non-biodegradable plastics in the environment and the use of non-renewable raw materials. For this reason, during recent years, there is a growing interest in so-called biodegradable polymers as alternative solution for the traditional petroleum-based polymers. Biodegradable polymers are polymers obtained from molecules of vegetable origin.

These biodegradable polymers shall be referred to, hereinafter, as biopolymers.

Among such biopolymers, the importance of polylactic acid is steadily growing. One of the driving forces of this invention is the fact that the production cost of L-lactic acid has been substantially reduced by high-volume production of crops such as corn, grains and potatoes . . . . Plastics or resins such as polylactic acid manufactured on the basis of these natural raw materials are characterized by a high strength and good transparency.

A drawback of polylactic acid for use as plastic in industrial applications is, however, the low impact resistance, as well as the brittleness and resulting lack of flexibility. These material features are caused, among others, by a high crystallinity and a rigid molecular structure of this polymer. Nevertheless, amorphous formulations of polylactic acid are also available; these, however, are equally brittle and hard. This disadvantage limits its use in a great number of applications, in particular, for use in film or packaging material on a large scale.

It is known in the art to compensate for this drawback by softening polylactic plastics or resins by incorporation of plasticisers, by applying co-polymerization, or by blending polylactic acid with more soft polymers.

The use of plasticisers in resins to increase their flexibility is a well-known method, and is not particularly limited to biopolymers. By the use of plasticisers the possibilities and applications for these polymers are substantially increased. Plasticisers are usually available in liquid form and can be used to process resins in various technical processes, such as injection moulding, thermoforming, blown film and cast film extrusion, rotational moulding, fibre spinning, filament processing. The plasticisers can be optimized for use in various polymers. More in particular, the polarity of a plasticiser can match the polarity of the polymer or polymer composition, so as to obtain an efficient interaction between these components, which results in a high plasticizing efficiency and a low migration of the plasticiser. Plasticisers are used in various polymers, among which the most important are: polyvinylchloride, polyamide, polar rubbers, polyurethane, and also biopolymers like polylactic acid.

As described in European patent EP 2 202 267 B1, filed by Daihachi Chemical Industry Co., Osaka, Japan, published Dec. 7, 2011, a known disadvantage of adding plasticisers is their tendency to migrate to the surface of the plastic. Various disadvantages result therefrom: the colour and the surface appearance is modified, the transparency of the plastic is reduced, and the fragility and brittleness of the plastic increase over time due to reduction of the plasticizing effect by the migration of the plasticiser from the bulk of the plastic to the surface (see e.g. paragraphs 4 and 5 of the text). This patent describes the use of mixed esters of a.m. succinic acid to minimize the migration from the PLA-polymer. The ester form of this patent, however, is not mentioned, contrary to other symmetric esters, such as butyldiglycol adipate. The properties of the latter compound, however, are less beneficial.

The scientific article published in SEI Technical Review, Number 66, April 2008, pages 50-54 entitled "Development of Elastic Polylactic Acid material Using Electron Beam Radiation", by Shinichi Kanazawa, describes the crystalline behaviour of polylactic acid and the 'bleeding out' of a plasticiser added to this compound. It confirms that, on the longer term, the polylactic acid based resin becomes brittle and hard.

The article does not specify plasticisers used. It discloses an electron-beam method to counter such bleeding-out phenomenon. Usually 10 to 30% by weight of the plasticiser should be added to the plastic so as to sufficiently reduce the glass transition temperature, usually to about room temperature.

Various plasticisers have been proposed in the state of the art to deal with this problem.

Japanese patent application No. 2000-198908, for example, discloses the use of acetyl tributyl citrate as plasticiser in polylactic acid.

In U.S. Pat. No. 8,232,354 B2, filed by Kao Corp. Tokyo, Japan, a method is described for the manufacture of plastic compounds on the basis of polylactic acid, wherein a polycarbodi-imide cross-linker has been added. The results of this compound in terms of plasticizing effects, however, were unsatisfactory.

U.S. Pat. No. 7,842,761, in the name of Lapol LLC, Santa Barbara, Calif., USA, describes a biological plasticiser for biopolymers such as polylactic acid, comprising a polyester plasticizing unit.

Column 1, lines 52 and following disclose the three basic techniques for plasticizing polymers of the polylactic acid type: addition of a plasticiser, co-polymerization and blending of flexible polymers.

More in particular, in this text, the drawbacks of the first two techniques are described.

U.S. Pat. No. 8,158,731 in the name of Hallstar Innovations Corp., Chicago, USA describes polymer blends comprising on the one part a biopolymer and on the other part an aliphatic polyester. The polyester is derived from repeating units of a dicarboxylic acid and an aliphatic diol.

As biopolymer, polylactic acid has been mentioned, for example on column 1, line 41. As dicarboxylic acids, for example, succinic acid and adipic acid have been mentioned (column 2, lines 13-14).

In the international patent application published as WO 2013/148255 in the name of 3M Innovative Properties Company, Saint Paul, Minn., USA, all claims are directed to citrate esters, comprising (amongst others) tetrahydrofurfuryl groups and a hydrogen or acyl group.

Reference is made e.g. to claim 13.

These plasticisers have been developed for use in 'suitable polymeric materials', see e.g. page 8, line 31, specifically mentioning polylactic acid. On page 8 the inventors extensively describe polylactic acid and on page 10 some commercial suppliers of this compound are set forth.

Page 7, lines 26-28 disclose that as well the citric acid as the tetrahydrofurfuryl alcohol may be produced by renewable raw materials. References to the preparation method for tetrahydrofurfuryl are set forth in the following lines.

Page 8 lines 20 and following describe the requirement of compatibility of the plasticiser with the polymer to be softened.

A suggestion is being made to the fact that the solubility nature of both compounds should be close to each other for a plasticiser to continue fulfilling its plasticizing function in the polymer.

Tri(alkyl)citrate has been mentioned on page 8, line 29.

Page 14, lines 23-29 describe the migration issue of the more traditional plasticisers when used in polylactic acid, and the fact that over time polylactic acid becomes brittle by the migration of the traditional plasticisers to the surface of the material (poor age stability).

In order to solve the problem of the migration of the plasticiser from the bulk of the polymer to the surface, a mixture could be used comprising plasticisers with quite different chemical structures. In such a case, however, other drawbacks appear: for example difficulties related to an appropriate and homogeneous mixing of these compounds in the biodegradable plastic, or their inherent incompatibility with the biopolymer.

The plasticisers known to be used in polymers such as polyvinylchloride do not necessarily act as plasticisers in polylactic acid in an acceptable manner: a minimal compatibility should be present between the plasticiser and the polymer to be plasticized. For this purpose, there should be a match between the chemical structure of the plasticiser and the polymer.

Problem and Aim of the Invention

The aim of the present invention is to solve the problems and overcome the above-mentioned drawbacks.

More in particular, the aim of the invention is to provide plasticisers that can be used to reduce the glass transition temperature Tg of biopolymers, more in particular, of biopolymers based on polylactic acid, to increase the elongation at break of these compounds, and to increase their flexibility.

The benefit resulting from the realization of this aim is to provide plasticized biodegradable resins, showing characteristics comparable to more traditional resins. Thanks to these characteristics, traditional resins may be effectively replaced on the market by such plasticized biodegradable resins.

Examples of these traditional plastics to be replaced comprise: polyethylene (PE), polypropylene (PP), thermoplastic elastomers, acrylonitrile-butadiene-styrene copolymers (ABS), polystyrene (PS), poly-ethylene-terephthalate (PET).

As mentioned above, although the use of plasticisers in biopolymers, and more specifically in polylactic acid may substantially enhance the flexibility, most of the plasticisers are characterized by a migration phenomenon to the surface of the plasticized biopolymer. This, in turn, results in a slowly increasing brittleness.

A more specific aim of the inventors is the development of new plasticisers with an increased compatibility and a low migration. By fulfilling such more specific aim, namely, the increase of the stability of plasticized biopolymers over time, and more in particular polylactic based polymers, biopolymers might become eligible for use in various new fields of application.

DESCRIPTION OF THE INVENTION

The invention relates to a composition comprising aliphatic polycarboxylic acid esters of formula (II) and of formula (I) or (III)

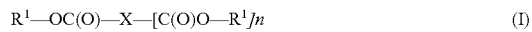

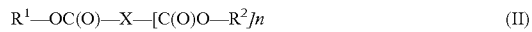

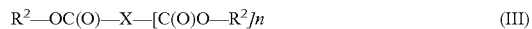

wherein
$R^1$ is a tetrahydrofurfuryl group, or a substituted tetrahydrofurfuryl group;
$R^2$ is an alkoxylated alkyl group, or a substituted alkoxylated alkyl group, different from $R^1$;
X is an alkyl group or a hydroxyl-substituted alkyl group comprising from 1 up to 4 C-atoms, and
n is 1 or 2.

These compositions are particularly useful as plasticisers in biodegradable polymers, more preferably in biodegradable aliphatic polyesters resins. The process ability of these polymers appears to be substantially enhanced by the use of the compositions set forth above.

If n is 2, [C(O)O—$R^1$] or [C(O)O—$R^2$] may be adhered to each C-atom of X.

According to a preferred embodiment of the invention, the alkoxylated alkyl group is derived from an ether alcohol selected from the following list: butyldiglycol (butoxethoxyethanol), butyltriglycolether (butoxyethoxyethoxyethanol), methyltriglycolether (methoxyethoxyethoxyethanol), butyldipropyleenglycol (butoxypropoxypropanol).

The term 'tetrahydrofurfuryl group' refers to either a 2- or a 3-tetrahydrofurfuryl group'. The structural formula of 2-tetrahydrofurfuryl alcohol is set forth below:

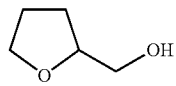

Its CAS number is 97-99-4 and empirical formula is $C_5H_{10}O_2$.

The term 'substituted tetrahydrofurfuryl group' refers to either a 2- or 3-tetrahydrofurfuryl group that is substituted with at least one alkyl or aryl group.

The number of substituents may vary according to the application and comprise any number in the range from 1 to 3. Suitable alkyl substituents may comprise from 1 to 15 carbon atoms, more preferably from 1 to 10, still more preferably from 1 to 3 or 5.

Preferred embodiments of the invention are set forth in the dependent claims of the present specification, as well as in the detailed description of the invention set forth hereinafter.

The compositions of this invention are novel and inventive over the earlier cited WO 2013/148255: indeed the esters disclosed in this specification apart from the tetrahydrofurfuryl group comprise a substituent denoted by $R^2$, (claim 1), $R^2$ or $R^4$ (claim 7) and $R^6$ (claim 13), wherein each of $R^2$, $R^4$ and $R^6$ represents hydrogen or an acyl group. The term 'acyl' is described on page 3, lines 5-9 of this specification as referring to a monovalent group of formula —(CO)$R^a$ where $R^a$ is an alkyl group and (CO) denotes a carbonyl group.

Thus, the compounds according to the present invention, comprising a (substituted) alkoxylated alkyl group, apart from the tetrahydrofurfuryl group, are neither disclosed, nor suggested in this earlier specification.

DETAILED DESCRIPTION OF THE INVENTION

The characterising feature of the composition according to the present invention is the presence of aliphatic polycarboxylic acid esters that comprise on the one hand a tetrahydrofurfuryl group or a substituted tetrahydrofurfuryl group, and on the other hand an alkoxylated alkyl group, or a substituted alkoxylated alkyl group.

These esters are referred to as 'asymmetrical esters' as will be clarified hereinafter. These esters may be present in the composition according to the invention, along with esters that comprise either tetrahydrofurfuryl groups or substituted tetrahydrofurfuryl groups alone, or alkoxylated alkyl groups, or substituted alkoxylated alkyl groups alone.

These esters are referred to as 'symmetrical esters' as will be clarified hereinafter. The compositions according to the present invention are thus characterised by the joint presence of specific symmetrical as well as asymmetrical esters.

According to a preferred embodiment, the polycarboxylic acid esters are obtained by esterification of either dicarboxylic acids, or tricarboxylic acids.

The compositions of the invention can be prepared by esterification of the aliphatic polycarboxylic acid with a selected mixture of different alcohols, wherein at least one alcohol comprises a tetrahydrofurfuryl group or a substituted tetrahydrofurfuryl group.

The term symmetrical ester in the context of the present invention is to be understood as an ester derived from a polycarboxylic acid, wherein all carboxylic acid groups are esterified with the same kind of alcohol.

An asymmetrical ester in the context of the present invention is to be understood as an ester derived from a polycarboxylic acid, wherein not all carboxylic acid groups are esterified with the same kind of alcohol.

In the case of a dicarboxylic acid such as e.g. succinic acid, glutaric acid or adipic acid, both carboxylic acid groups are esterified with the same alcohol in case of a symmetrical ester, and are esterified with a mixture of at least 2 different alcohols in case of an asymmetrical ester.

When the aliphatic polycarboxylic acid is an aliphatic dicarboxylic acid, the preparation method set forth supra yields on the one hand symmetrical esters, i.e. esters comprising a tetrahydrofurfuryl group or a substituted tetrahydrofurfuryl group at either side, or an alkoxylated alkyl group, or substituted alkoxylated alkyl group at either side, and on the other hand asymmetrical esters, comprising a tetrahydrofurfuryl group or a substituted tetrahydrofurfuryl group at one side and an alkoxylated alkyl group, or substituted alkoxylated alkyl group at the other side.

In the case of a tricarboxylic acid, such as e.g. citric acid or trimellitic acid, the asymmetrical ester is obtained by esterification of one carboxylic acid group with one type of alcohol, and both of the other carboxylic acid groups are esterified with the other type of alcohol.

Application:

The composition of the present invention is in particular useful as plasticiser, more preferably as plasticiser for biodegradable polyester resins.

The term biopolymers in the context of the present invention should be understood as comprising polymers that are manufactured in a synthetic manner from monomers of biological origin. More in particular, the succinate, according to the invention, can be used as plasticiser in such biodegradable polymers on the basis of aliphatic polyesters, as well homo- as copolyesters. Still more in particular, the succinate can be used as plasticiser in biopolymers on the basis of polylactic acid (PLA).

The term polylactic acid, as used in the context of the present invention, relates to a polymer or copolymer comprising at least 50 mol % of lactic acid monomer units.

Examples of such polylactic acids comprise, but are not restricted to:

(a) a homopolymer of polylactic acid, (b) a copolymer of lactic acid with one or more aliphatic hydroxycarbon acids, different from lactic acid, (c) a copolymer of lactic acid with an aliphatic polyhydric alcohol and an aliphatic polycarboxylic acid, (d) a copolymer of lactic acid with an aliphatic polycarboxylic acid, (e) a copolymer of lactic acid with an aliphatic polyhydric alcohol, and (f) a mixture of two or more of (a)-(e) as above mentioned. Examples of lactic acid comprise L-lactic acid, D-lactic acid, a cyclic dimer hereof (L-lactide, D-lactide or DL-lactide) and mixtures hereof. Examples of the hydroxycarboxylic acid that can be used in the above-mentioned copolymers (b) and (f) comprise, but are not restricted to, for example: glycolic acid, hydroxybutyric acid, hydroxyvaleric acid, hydroxyhexanoic acid and hydroxyheptanoic acid, as well as combinations hereof.

Furthermore, the biodegradable or bio-renewable thermoplastic materials wherein the succinate according to the invention might be used as plasticiser, may consist of a single thermoplastic material such as a polymer (for example polylactic acid alone), but they might also consist of a mixture of polylactic acid with at least one additional thermoplastic material. In such a preferred embodiment, the biodegradable or bio-renewable thermoplastic material may comprise a blend or mixture of polylactic acid with one or more aliphatic polyesters or copolyesters like polybutylene succinate, polyhydroxy alkanoates (PHA), starch, cellulose or another polysaccharide or combinations hereof.

In still another preferred embodiment the biodegradable or bio-renewable material may comprise a blend or mixture of polylactic acid with at least one aliphatic polyester (e.g. polybutylene succinate) or copolyester, a mixture of polylactic acid with at least one polyhydroxy alkanoate (PHA), or a blend of polylactic acid with another biopolymer such as starch, cellulose or another polysaccharide. In a still more preferred embodiment, the biodegradable or bio-renewable thermoplastic material may comprise a mixture of polylactic acid, at least one PHA and at least one starch. In some embodiments, the thermoplastic material may be present in about 5 to about 95% by weight, calculated on the basis of the total weight of the composition. In some embodiments, the amount of polylactic acid, as compared to the total amount of thermoplastic material in the composition, is comprised between approximately 15 to approximately 100% by weight, and, in other embodiments, is comprised between approximately 30 to approximately 100% by weight calculated in relation to the total weight of thermoplastic material.

Mode of Preparation:

The composition and the esters according to the invention may be prepared according to the process described hereinafter.

As a first step, a mixture is prepared of the alcohols selected in the appropriate concentration, depending on the intended application, and wherein at least one of the alcohols comprises a tetrahydrofurfuryl group. This group may be substituted. These alcohols are introduced into a reactor, followed by heating up to approx. 90° C. and addition of the aliphatic polycarboxylic acid or the corresponding anhydride in an amount such that the ratio of the carboxylic acid over the alcohol mixture is approximately 1:2 in case a dicarboxylic acid is used, and to approximately 1:3 in case a tricarboxylic acid is used.

The use of an excess amount of alcohol and the use of a dehydrating agent or azeotropic agent may be of advantage to finish the reaction.

(A dehydrating agent is to be understood as an auxiliary compound that serves to remove the excess water obtained as by-product during the esterification. This is not an additive for the resin composition, only an auxiliary compound in this process step during the esterification.)

As a catalyst, use can be made e.g. of a strong acid, such as sulphuric acid.

The reaction is considered to be finished when no water is formed any more. After neutralization of the catalyst, the possible excess amount of alcohol is removed by distillation. The mixture may be washed to remove possible impurities. As a supplementary step, the ester can be discoloured by means of discoloration techniques known per se, such as: the use of active carbon, oxidation with hydrogen peroxide, hydrogenation with hydrogen, . . . . Finally, the product is dried by heating at increased temperature (80 up to 150° C.) under vacuum.

An alternate mode of preparation for the process described above, namely the esterification of a carboxylic acid and an alcohol, is the reaction of the carboxylic acid with a different functional group such as an alkyl chloride.

Effects of the Invention

The most surprising effect of the compositions according to the invention is the low volatility in polyester resins, in particular those comprising or based upon polylactic acid, as compared to e.g. a symmetric ester of a polycarboxylic acid such as dibutoxyethoxyethyladipate, in spite of a higher vapour pressure of this compound. Moreover, when the compositions of the invention are used as plasticiser in e.g. polylactic acid, in particular when used in film products, significantly improved properties are observed, such as e.g. the absence of smell and the absence of greasiness on the film surface.

Although the inventors cannot give an assurance as to the scientific exactness of this phenomenon, they believe that this surprising effect is resulting from an improved compatibility of this plasticiser with the hydrophilic, polar nature of polylactic acid.

By way of example, hereinafter is set forth a specific compound that may be present in the compositions of the invention.

Tetrahydrofurfuryl-butoxyethoxyethyl-succinate (THF-BEES), molecular weight 346.

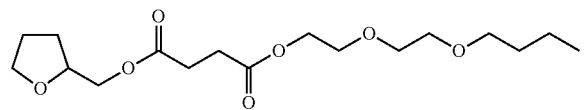 [SMILES: CCCCOCCOCCOC(=O)CCC(=O)OCC1CCCO1]

This compound may also be denoted as tetrahydrofurfuryl-butyldiglycol-succinate.

The mixtures of alcohols suitable for use in the present invention may comprise, apart from tetrahydrofurfurylalcohol, as such or substituted, one or more alkoxylated alcohols, such as butoxyethoxyethanol, butoxyethanol, methyltriglycolether as well as isomers and mixtures of these compounds.

The process of ethoxy- or propoxylation is known as such for the person skilled in the art.

The ethoxylation or propoxylation process yields alcohols whereby the corresponding esters are more polar and as such are more compatible with polar polymers, such as some biodegradable aliphatic polyester resins.

Ethyleneoxyde, polyethyleneoxyde, propyleneoxyde or polypropyleneoxyde have an average chain length of 2 to approx. 8 mol of oxygen per mol of alcohol.

An extra benefit resulting from the addition of an oxygen is the increase of the molecular weight and a substantial reduction of the VOC in combination with the increase in compatibility with the biodegradable polymer.

The ester, according to the invention, is in particular suitable for use as plasticiser in various polymers, and more specifically in biopolymers. Examples of polymers wherein the ester can be used as plasticiser are aliphatic polyester resins (for example polylactic acid and polybutylene succinate), cellulose esters, polyvinylchloride, polyvinylbutyral, polar rubbers, polyurethanes and acrylate polymers such as poly(methyl methacrylate).

Aliphatic polyesters may be produced according to the dehydration-polycondensation reaction of one or more aliphatic hydroxycarboxylic acids or their dehydrated cyclic analogues (lactones and lactides). Examples of hydroxycarboxylic acids are L-lactic acid, D-lactic acid, glycolic acid, hydroxy-butyric acid, hydroxy-valeric acid, hydroxy-pentanoic acid, hydroxy-hexanoic acid, hydroxy-heptanoic acid, . . . .

According to an alternative method the aliphatic polyesters may be manufactured by a dehydration-polycondensation reaction of a mixture comprising an aliphatic polycarboxylic acid and an aliphatic diol, such as polybutylene succinate. Examples of such compounds are mentioned in the already cited PCT publication WO 2013/148255.

The term polylactic acid, as used in the context of the present invention, relates to a homopolymer of lactic acid or a copolymer of lactic acid with a hydroxycarboxylic acid or a polymer composition containing either the homopolymer of lactic acid or a copolymer of lactic acid with a hydroxycarboxylic acid. By the presence of a chiral core in lactic acid, the molecular structure of lactic acid in the polylactic acid can be either L-lactic acid or D-lactic acid, or a mixture of both in various possible concentrations. The choice of the cyclic monomer used in the polymerization reaction to produce polylactic acid determines, together with the choice of the plasticiser, the concentration of the plasticiser in the polymer and the processing conditions for incorporation of the plasticiser in the polymer, the final properties of the polymer. For the polymerization reaction to polylactic acid, use is, preferably, made of lactide, i.e., the cyclic monomer comprising two molecules of lactic acid that are dehydrated. This lactide can be either L,L-lactide (2 molecules of L-lactic acid), as well as D,D-lactide (2 molecules of D-lactic acid) or meso-lactide (1 molecule of L-lactic acid and 1 molecule of D-lactic acid).

The average molecular weight of the polylactic acid is, preferably, from about 10 000 up to 1 000 000, more preferably, from about 30 000 to about 600 000, and still more preferably, from about 50 000 to about 400 000. Polylactic acid, with an average molecular weight between the above-mentioned limits, has usually a sufficient mechanical strength and a good process ability.

Examples of commercially available polylactic acids are "Ingeo" of Natureworks, "Purasorb" from Corbion Purac, "Lacty", marketed by Shimadzu Corp., "Lacea", marketed by Mitsui Chemicals Inc., "Terramac", marketed by Unitika Ltd., "eco-PLA" marketed by Cargill-Dow LLC, USA, "Ecologe", marketed by Mitsubishi Plastics Inc.

When used as plasticiser, the ester according to the present invention usually functions as primary plasticiser. According to a more specific embodiment, other plasticisers may be added to the biopolymer, whereby the ester, according to the invention, may then function either as primary or secondary plasticiser.

According to a preferred embodiment of the present invention, the amount of polylactic acid in the plastic composition is at least 50% of the total weight of the composition, and according to a still more preferred embodiment, at least 60%.

So as to obtain a sufficient level of mechanical strength, impact resistance and flexibility, the amount of ester in the plastic composition, according to the present invention, amounts to 2 to 50%, more preferably from 2 to 20%. In more durable consumption products such as the housing or casing of electrical appliances and automotive parts, the amount should preferably not exceed 25%. In products that require a high degree of flexibility such as films for use in agricultural applications or for packaging, the amounts are preferably comprised between 5 and 40%.

The resin composition, according to this invention, may, apart from the plasticiser, comprise one or more other ingredients such as, for example, inorganic fillers and silicates, such as talc, china clay, montmorillonite, silica, magnesium oxide, titanium oxide, calcium carbonate, magnesium hydroxide, fibre glass, carbon fibers, graphite powder, etc.

The resin composition according to this invention may apart from the plasticiser also comprise one or more other ingredients added so as to optimize the resin composition in view of the anticipated application. These ingredients may comprise flame retardants, hydrolysis-retardants, a lubricant, an antistatic agent, antifogging agents, light stabilizers, UV-absorbers, fungicidal additives, antimicrobial additives, foaming agents, . . . .

Preparation of the Resin Composition:

An amount of polylactic acid Ingeo 2003D (extrusion quality) grains were dried during 24 hours in an oven at 70° C. and subsequently introduced in a Brabender-mixing device. The amount of PLA was chosen so as to obtain an amount of 55 g of resin material. PLA was then heated at a temperature of around 190° C. and stirred at a speed of 50 revolutions per minute.

After 5 minutes the plasticiser was added, and the mixture was further stirred for a total duration of 15 minutes. Afterwards, the mixture was cooled.

Preparation of Films (10 cm*10 cm*450 μm)

Films were prepared by means of an Agila PE20 hydraulic press. 7.5 g of the resin composition containing the ester compound, as previously described, was pressed at a temperature of 170° C. The contact time was initially 4 minutes, followed by 3 minutes 20 seconds at 10 bar and 2 minutes 30 seconds at 150 bar with two degassing cycles; after this, cooling with water took place at 50 bar for the period of 3 minutes.

Evaluation of the ester mixture as plasticiser for PLA by means of DSC:

Analysis conditions:

Equilibration at −20° C. for 2 min;

First heating cycle from −20° C. to 200° C. at a speed of 10° C./min;

Cooling from 200° C. to −40° C. at a speed of 10° C./min;

Second heating from −40° C. to 200° C. at a speed of 10° C./min.

Evaluation of the films took place on the basis of a visual inspection, odour, greasy appearance of the film surface, weight loss at 60° C. after 7 days.

For the evaluation, the following codes were used:

1=total absence;
2=little;
3=noticeable by visual inspection;
4=clearly visible by visual inspection;
5=large amounts visible.

TABLE

Evaluation of PLA 2003D with plasticiser

| | | | Film evaluation | | |
|---|---|---|---|---|---|
| Plasticiser | Conc | DSC Tg (° C.) | Visual | odour | Greasy surface | Weight loss (%) |
| none | | 61.8 | transparent | 1 | 1 | 0.25 |
| Di(butyldiglycol)adipate | 15% | 30.3 | transparent | 4 | 2 | 1.64 |
| Di(butyldiglycol)succinate | 15% | 30.0 | transparent | 4 | 2 | 0.22 |
| Di(tetrahydrofurfuryl)succinate | 15% | 30.2 | transparent | 2 | 1 | 0.33 |
| Tetrahydrofurfuryl-butyldiglycol-succinate | 15% | 26.2 | transparent | 1 | 1 | 0.30 |
| Di(benzyl)succinate | 15% | 31.5 | transparent | 4 | 5 | 0.50 |
| Tetrahydrofurfuryl-butyldiglycol-citrate | 15% | 29.5 | transparent | 1 | 1 | 0.97 |

From the above tests it is clear that the use of the new compounds according to the invention, i.e. tetrahydrofurfuryl-butyldiglycol-succinate and tetrahydrofurfuryl-butyldiglycol-citrate, yield significantly improved results as compared to the results resulting from the use of the comparative compounds.

The invention claimed is:

1. A composition comprising:
a) a biodegradable resin; and
b) a plasticiser of aliphatic dicarboxylic acid esters of formula (II) and of formula (I) or (III)

$$R^1\!-\!OC(O)\!-\!X\!-\![C(O)O\!-\!R^1] \quad (I)$$

$$R^1\!-\!OC(O)\!-\!X\!-\![C(O)O\!-\!R^2] \quad (II)$$

$$R^2\!-\!OC(O)\!-\!X\!-\![C(O)O\!-\!R^2] \quad (III)$$

wherein
$R^1$ is a tetrahydrofurfuryl group, or a substituted tetrahydrofurfuryl group;
$R^2$ is an alkoxylated alkyl group, or a substituted alkoxylated alkyl group, different from $R^1$;
$R^2$ is butyldiglycolate; and
X is an alkyl group or a hydroxyl-substituted alkyl group comprising from 1 up to 4 C-atoms.

2. A biodegradable aliphatic polyester resin composition comprising a composition comprising:
a) a biodegradable resin; and
b) a plasticiser of aliphatic dicarboxylic acid esters of formula (II) and of formula (I) or (III)

$$R^1\!-\!OC(O)\!-\!X\!-\![C(O)O\!-\!R^1] \quad (I)$$

$$R^1\!-\!OC(O)\!-\!X\!-\![C(O)O\!-\!R^2] \quad (II)$$

$$R^2\!-\!OC(O)\!-\!X\!-\![C(O)O\!-\!R^2] \quad (III)$$

wherein
$R^1$ is a tetrahydrofurfuryl group, or a substituted tetrahydrofurfuryl group
$R^2$ is an alkoxylated alkyl group, or a substituted alkoxylated alkyl group, different from $R^1$; and
X is an alkyl group or a hydroxyl-substituted alkyl group comprising from 1 up to 4 C-atoms.

3. The biodegradable aliphatic polyester resin composition of claim 2, wherein the biodegradable aliphatic polyester resin is at least one member selected from the group consisting of resins obtained by condensation of hydroxycarboxylic acid(s) and resins obtained by condensation of aliphatic dicarboxylic acid(s) and aliphatic diols.

4. The biodegradable aliphatic polyester resin composition of claim 2, comprising a homo- or copolymer of a polylactic acid and/or a polybutylene succinate.

5. The biodegradable aliphatic polyester resin composition of claim 2 includes a polylactic acid.

6. A composition comprising:
a) a biodegradable resin; and
b) a plasticiser of aliphatic dicarboxylic acid esters of formula (II) and of formula (I) or (III)

$$R^1\!-\!OC(O)\!-\!X\!-\![C(O)O\!-\!R^1] \quad (I)$$

$$R^1\!-\!OC(O)\!-\!X\!-\![C(O)O\!-\!R^2] \quad (II)$$

$$R^2\!-\!OC(O)\!-\!X\!-\![C(O)O\!-\!R^2] \quad (III)$$

wherein
$R^1$ is a tetrahydrofurfuryl group, or a substituted tetrahydrofurfuryl group; $R^2$ is an alkoxylated alkyl group, or a substituted alkoxylated alkyl group, different from $R^1$; and
X is an alkyl group or a hydroxyl-substituted alkyl group comprising from 1 up to 4 C-atoms
wherein the composition is obtained by esterification of an aliphatic dicarboxylic acid with a mixture of tetrahydrofurfuryl alcohol and one or more alcohols selected from the following: butoxyethoxyethanol, butoxyethoxyethoxyethanol, methoxyethoxyethoxyethanol, and butoxypropoxypropanol.

7. The composition of claim 6, wherein the aliphatic dicarboxylic acid includes succinic acid.

8. A biodegradable aliphatic polyester resin composition comprising the composition of claim 1.

9. The biodegradable aliphatic polyester resin composition of claim 8, wherein the biodegradable aliphatic polyester resin is at least one member selected from the group consisting of resins obtained by condensation of hydroxycarboxylic acid(s) and resins obtained by condensation of aliphatic dicarboxylic acid(s) and aliphatic diols.

10. The biodegradable aliphatic polyester resin of claim 8, comprising a homo- or copolymer of a polylactic acid and/or a polybutylene succinate.

11. A biodegradable aliphatic polyester resin composition comprising the composition of claim 6.

* * * * *